United States Patent [19]

Hofmann

[11] Patent Number: 4,464,399
[45] Date of Patent: Aug. 7, 1984

[54] OCTODIOL, A SOLVENT FOR DIRECT DISSOLUTION OF CHOLESTEROL GALLSTONES

[75] Inventor: Alan F. Hofmann, La Jolla, Calif.

[73] Assignee: The Regents of the University of California, Berkeley, Calif.

[21] Appl. No.: 506,424

[22] Filed: Jun. 21, 1983

[51] Int. Cl.³ .................... A61K 31/08; A61K 31/10; A61K 31/16

[52] U.S. Cl. ................... 424/342; 424/320; 424/337

[58] Field of Search ................ 424/320, 337, 342

[56] References Cited

U.S. PATENT DOCUMENTS 4,205,086 5/1980 Babayan .............................. 424/312

FOREIGN PATENT DOCUMENTS 1029610 5/1966 United Kingdom .

OTHER PUBLICATIONS

Chemical Abstracts, vol. 65, 5368c (1966).

*Primary Examiner*—Jerome D. Goldberg
*Assistant Examiner*—Joyce L. Morrison
*Attorney, Agent, or Firm*—Joseph E. Mueth

[57] ABSTRACT

The use of a compound having the general formula:

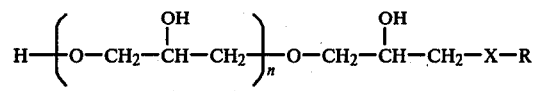

wherein n is 0 or a small integer, normally from 1 to 3; R is an alkyl or alkenyl group containing from 4 to 18 carbon atoms; and X is oxygen, sulfur or amide

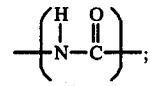

with the further proviso that any one or more of the OH groups can be replaced by a polar zwitterionic group such as $NH_4+$ $SO_3-$; for the treatment of cholesterol gallstones by infusion of the solvent around the gallstones to dissolve them.

6 Claims, No Drawings

OCTODIOL, A SOLVENT FOR DIRECT DISSOLUTION OF CHOLESTEROL GALLSTONES

This invention was made with Government support under Grant No. AM21506 awarded by the Department of Health and Human Services.

BACKGROUND OF THE INVENTION

It is known that gallstones occur in the biliary tract and that the majority of these gallstones are composed of cholesterol. Access to the biliary tract may be obtained endoscopically, or after surgery by a T-tube.

In the past, organic solvents, such as ether or chloroform, have been used; but these are poorly tolerated by patients. Controlled studies reporting efficacy have not appeared in the medical literature. Five years ago, Dr. Alan F. Hofmann, then at the Mayo Clinic, in collaboration with Dr. Gordon Flynn and Dr. William I. Higuchi of the College of Pharmacy of the University of Michigan, found that mono-octanoin was an excellent solvent for cholesterol. Subsequently, they learned that this material was available as a commercial emulsifier (Capmul), manufactured by Capitol City Products, a subsidiary of Stokely Van Camp, Inc. In subsequent work, these investigators showed that this compound could be infused into T-tubes and would cause gallstone dissolution in some patients.

U.S. Pat. No. 4,205,086, issued May 27, 1980, covers the use of fatty acids and/or alcohol esters thereof, specifically, glyceryl-1-monooctanoate (monooctanoin, which is referred to above by the tradename Capmul). The physical properties and clinical application to monooctanoin is disclosed in Gastroenterology 78:1016-1022, 1980.

SUMMARY OF THE INVENTION

Briefly, the invention comprises the use of a compound having the general formula:

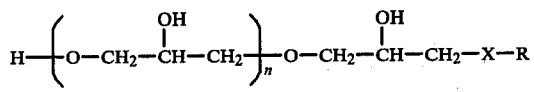

wherein n is 0 or a small integer, normally from 1 to 3; R is an alkyl or alkenyl group containing from 4 to 18 carbon atoms; and X is oxygen, sulfur or amide

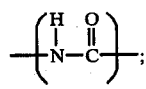

with the further proviso that any one or more of the OH groups can be replaced by a polar zwitterionic group such as $NH_4^+$ $SO_3^-$; for the treatment of cholesterol gallstones by infusion of the solvent around the gallstones to dissolve them.

R may be butyl, decyl, dodecyl, pentenyl and the like.

It is an object of this invention to provide a novel method for the treatment of gallstones.

More particularly, it is an object of this invention to provide a novel class of solvents for the direct dissolution of cholesterol gallstones.

These and other objects and advantages of the invention will be apparent from the detailed description which follows.

DESCRIPTION OF PREFERRED EMBODIMENTS

The preferred solvent has the following composition:

"octodiol"

It is an excellent solvent for cholesterol (cholesterol solubility is 230 mg/ml). The solvent is not hydrolyzed by lipases in the gastrointestinal tract. The solvent is infused by T-tubes or endoscopically around cholesterol gallstones in patients to dissolve them.

The advantages of the octodiol is that it is not hydrolyzed by enzymes in the digestive tract and is absorbed intact. It is believed that this compound is less destructive to epithelial surfaces. However, the most important advantage is that the compound has a far greater solubility for cholesterol than any compound proposed for this purpose to date; and in an in vitro model for gallstone dissolution, it dissolves gallstones more rapidly than the existing solvents.

The drug can also be the monothiooctyl ether of glycerol and the like.

EXAMPLE

A solution of 1-octanol ($2.42 \times 10^{-1}$ moles) in 135 ml of freshly distilled tetrahydrofuran (THF) was added to a stirring suspension of NaH ($2.91 \times 10^{-1}$ moles) in 90 ml of THF. Allyl bromide ($2.91 \times 10^{-1}$ moles) was then added dropwise. Mild effervescence was observed. The resulting solution was heated to to reflux for 30 minutes. The reaction was quenched by very slow addition of 180 ml of 1.0N HCl to the ice cooled white opaque mixture. The mixture was decanted into a separatory funnel and the organic layer removed. The aqueous layer was extracted repeatedly with $Et_2O$. The combined organic layers were washed with brine and dried over magnesium sulfate. The solvent was removed in vacuo leaving a yellow liquid. The product mixture was subjected to distillation, the allyl-n-octyl ether was collected at 185° C. Yield: 94.6%.

A 3-liter three-necked flask equipped with a thermometer and an additional funnel is charged with the allyl n-octyl ether dissolved in 370 mls dry $CH_2Cl_2$ (passed through alumina and stored over 4 Å sieves). The mixture is stirred and the temperature is kept below 25° C. by cooling (ice bath) as required during the addition over 45 minutes of a solution of meta-chloroperbenzoic acid in 640 mls of $CH_2Cl_2$. The mixture was allowed to stir overnight at room temperature, during which time the mixture became opaque white. The solution was filtered and the solute was poured into a separatory funnel where it was washed with $3 \times 500$ ml 10% sodium sulfite solution, $3 \times 500$ ml 5% $NaHCO_3$, $3 \times 500$ ml $H_2O$, $3 \times 500$ ml brine and then dried over $MgSO_4$. Solvent was removed yielding 32.1 gr of a slightly yellow liquid which was the glycidyl ether of 1-octanol, an epoxide. Yield=>75.4%.

A $1.73 \times 10^{-1}$ mole sample of the epoxide in 400 mls THF and 215 mls $H_2O$ was stirred while 15 mls of 8% (wt/vol.) perchloric acid was added. After 24 hours brine was added and the mixture extracted several times with ether. The organic phase was washed c̄ dilute sodium bicarbonate and brine, dried over ($Na_2SO_4$) and the and the solvent removed using a rotary evaporation to give the crude monoctyl ether of glycerol. The diol was then dissolved in 100 mls of heptane and refrigerated at −20° C. for 48 hours, after which time the diol precipitates out a very fine, white, crystalline mass. The solution was rapidly filtered through a Büchner funnel. The diol is a liquid at room temperature.

The superior cholesterol dissolving ability of octodiol is shown by the data depicted in the drawing. The data depicted in the drawing was obtained using five cholesterol gallstones from a human patient. The gallstones tested had the following initial weights before attempting dissolution with the solvents indicated:

| SOLVENT | STONE WEIGHT |
|---|---|
| octodiol | 149 mg |
| Campmul | 147 mg |
| (mostly glyceroyl-1-monooctanoate) | |
| 1 - octanol | 144 mg |
| "octanol" | |
| Octanoate ester of | 152 mg |
| 1,2-propylene glycol | |
| "Prop-2-ol-1-oct" | |
| Control (water) | 133 mg |

In each case 5 ml of human bile was first mixed with 5 ml of the indicated solvent and the mixture added to the gallstone in a small bottle, which was then rotated gently. The gallstone was removed after 100 minutes and again after 200 minutes, dried and weighed. The curves show the percentage of the gallstone which dissolved in each solvent at the times indicated. The superiority of octodiol is apparent.

The drug is normally infused into the patient in the form of the liquid, either neat or containing a small addition of water (which may further increase the solubility of cholesterol). The drug is present in the solution in an amount of from 70 to 100% by weight of the solution. The drug is usually administered by infusion, although other techniques of administration can be used. In any case, the drug is used in an amount effective to dissolve the gallstone which is usually about 1–5 ml/hour for a 150 mg stone. More or less can be used as will be apparent to those skilled in the art.

Having fully described the invention it is intended that it be limited only by the lawful scope of the appended claims.

I claim:

1. The method of treating gallstones in a human afflicted with gallstones which comprises administering to said human by infusion around the gallstones to dissolve them, an effective amount for treating gallstones, of the monooctyl ether of glycerol having the formula $C_8H_{17}OCH_2CHOHCH_2OH$.

2. The method of claim 1 wherein the drug is used in an effective amount on the order of 1 to 5 ml per hour per 150 mg of gallstone.

3. The method of claim 1 wherein the drug is administered neat.

4. The method of claim 1 wherein the drug is administered together with a small amount of water.

5. The method of claim 1 wherein the drug is infused by T-tubes.

6. The method of claim 1 wherein the drug is infused endoscopically.

* * * * *